United States Patent [19]
Schefczik

[11] 4,096,145
[45] Jun. 20, 1978

[54] NAPHTHOLACTAM DERIVATIVES

[75] Inventor: Ernst Schefczik, Ludwigshafen, Germany

[73] Assignee: BASF Aktiengesellschaft, Ludwigshafen am Rhein, Germany

[21] Appl. No.: 776,943

[22] Filed: Mar. 14, 1977

[30] Foreign Application Priority Data

Mar. 19, 1976 Germany .............................. 2611665

[51] Int. Cl.$^2$ .................. C07P 1/384; C07D 401/04; C07D 471/04
[52] U.S. Cl. ........................ 260/281 GN; 260/281 R; 260/282; 260/287 C; 260/287 F; 260/294.8 B; 260/295 T; 544/32; 544/126; 544/127; 544/131; 8/177 R; 8/179; 8/180; 8/1 D; 544/252; 544/248; 544/282; 544/250
[58] Field of Search ......... 260/281 GN, 282, 247.1 L, 260/326.27; 544/126, 127, 131

[56] References Cited

U.S. PATENT DOCUMENTS 3,892,750 7/1975 Frey .................................. 260/270 Q

OTHER PUBLICATIONS

Brack et al., Chem. Abs. 83, 12204w (1975).
Schefczik, Chem. Abs. 84, 107077s (1976).

*Primary Examiner*—Donald G. Daus
*Assistant Examiner*—Mark L. Berch
*Attorney, Agent, or Firm*—Keil, Thompson & Shurtleff

[57] ABSTRACT

Compounds of the formula

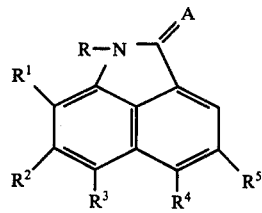

where A is a heterocyclic group containing a pyridone moiety and R to $R^5$ are each hydrogen or substituents conventionally encountered in dyes. The compounds are eminently suitable for coloring resins and for dyeing textile materials, particularly polyester textile materials.

13 Claims, No Drawings

NAPHTHOLACTAM DERIVATIVES

The present invention relates to compounds of the formula I

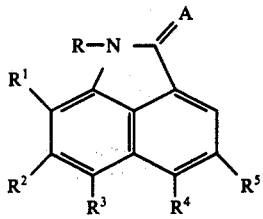

where A is a radical of the formula

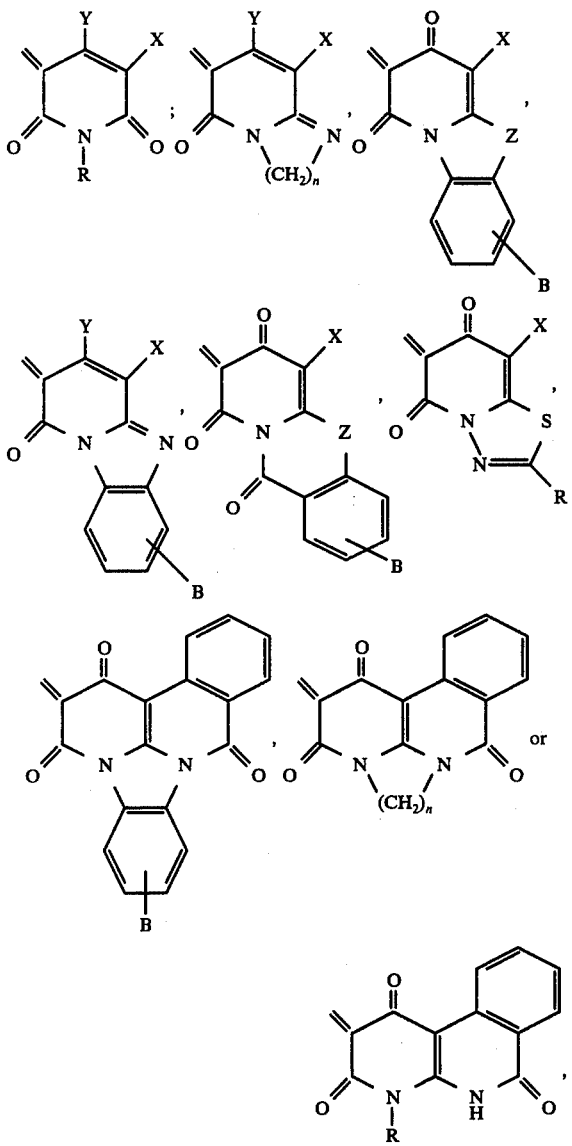

$n$ is 2 or 3, R is hydrogen or unsubstituted or substituted alkyl, cycloalkyl, aralkyl or aryl, $R^1$ is hydrogen, chlorine, bromine, alkyl, alkoxy, $NO_2$ or arylmercapto, $R^2$ is hydrogen or chlorine, $R^3$ is hydrogen, chlorine, bromine, alkyl, alkoxy, nitro, acylamino, alkylsulfonylamino, arylsulfonylamino, alkylmercapto, arylmercapto, arylsulfonyl, alkylsulfonyl, unsubstituted or N-substituted sulfamide, alkanoyl or aroyl, $R^4$ is hydrogen, chlorine, alkoxy, arylmercapto or alkylmercapto, or $R^3$ and $R^4$ together are a radical of the formula

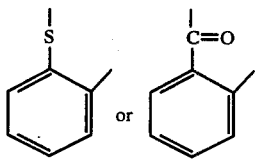

$R^5$ is hydrogen, chlorine or alkoxy, B is hydrogen, methyl, methoxy or chlorine, X is cyano or unsubstituted or substituted carbamoyl, Y is hydrogen, hydroxyl, alkyl of 1 to 4 carbon atoms, chlorine, bromine, $C_1$ to $C_4$ alkoxycarbonyl or unsubstituted or N-substituted carbamoyl, or X and Y together are a radical of the formula

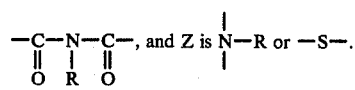

More particularly, R is alkyl of 1 to 8 carbon atoms, hydroxyalkyl of 2 or 3 carbon atoms, alkoxyalkyl of 3 to 8 carbon atoms, β-chloroethyl, β-cyanoethyl, alkoxycarbonylethyl, where alkoxy is of 1 to 4 carbon atoms, carbamoylethyl, N-monosubstituted or N,N-disubstituted alkylcarbamoylethyl, where alkyl is of 1 to 4 carbon atoms, cyclohexyl, benzyl, phenylethyl or phenyl.

Specific examples of R are propyl, butyl, hexyl, β-ethylhexyl, β-hydroxyethyl or β-hydroxypropyl, methoxyethyl, ethoxyethyl, methoxypropyl, ethoxypropyl, butoxypropyl, amyloxypropyl, methoxycarbonylethyl, ethoxycarbonylethyl or butoxycarbonylethyl and preferably methyl, ethyl or β-cyanoethyl.

Examples of alkyl, alkoxy and arylmercapto groups $R^1$ are methyl, ethyl, methoxy, ethoxy and phenylmercapto which is unsubstituted or substituted by chlorine, methyl, methoxy, phenyl, phenoxy or methoxycarbonyl.

Examples of $R^3$ are the same radicals as those mentioned for $R^1$, as well as naphthylmercapto, acylaminophenylmercapto, diacylaminophenylmercapto, acetylamino, propionylamino, benzoylamino which is unsubstituted by chlorine, methyl or methoxy, methylsulfonylamino, ethylsulfonylamino, phenylsulfonylamino, tolylsulfonylamino, methylmercapto, ethylmercapto, β-hydroxyethylmercapto, β-hydroxypropylmercapto, butylmercapto, methylsulfonyl, ethylsulfonyl, phenylsulfonyl, tolylsulfonyl, chlorophenylsulfonyl, acetyl, chloroacetyl, propionyl, butyryl, benzoyl which is unsubstituted or substituted by methyl, methoxy, chlorine or bromine, sulfamoyl, N-methyl-, N-ethyl-, N-butyl-, N-phenyl-, N-chlorophenyl-, N-methylphenyl-, N-methoxyphenyl-, N-trifluoromethylphenyl-, N-methyl-N-phenyl-, N,N-dimethyl-, N,N-diethyl-, N,N-dipropyl- and N,N-dibutyl-sulfamoyl, pyrrolidinosulfonyl, piperidinosulfonyl or morpholinosulfonyl. $R^3$ may also be a radical of the formula $NHCONH_2$, $NHCONHCH_3$ or $NHCONHC_6H_5$.

$R^4$ may be hydrogen, chlorine, or one of the alkoxy, alkylmercapto and arylmercapto radicals mentioned for $R^1$.

Examples of alkoxy radicals $R^5$ are methoxy and ethoxy. Examples of N-substituted carbamoyl radicals Y are CONHCH₃, CONHC₂H₅, CONHC₄H₉, CONHC₂H₄OH, CON(CH₃)₂, CON(C₃H₇)₂, CON(C₄H₉)₂ and

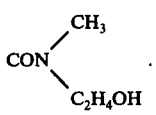

The compounds of the formula I may be manufactured by reacting compounds of the formula II

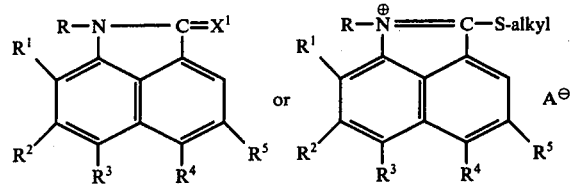

where X¹ is oxygen or sulfur and A⊖ is an anion, and alkyl is of 1 to 4 carbon atoms, with compounds of the formula A—H₂.

If X¹ is O, a condensing agent must be present, whilst if X¹ is S or the compounds containing the S-alkyl groups are used, this is not necessary.

Suitable condensing agents are phosphorus halides, eg. phosphorus pentachloride, phosphorus trichloride, phosphorus oxytribromide and especially phosphorus oxytrichloride.

The reaction may be carried out in an inert solvent, eg. a glycol diether or polyglycol diether, butyrolactone, toluene, chlorobenzene, dichlorobenzene, nitrobenzene or dioxane, or in an excess of the condensing agent.

If the reaction of the naphtholactam derivatives is carried out without a condensing agent, the above solvents may again be used; additional examples of suitable solvents are pyridine, glacial acetic acid, dimethylformamide or N-methylpyrrolidone.

The compounds of the formula

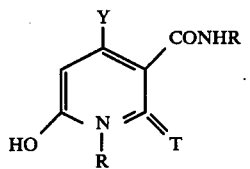

where T is oxygen and R and Y have the stated meanings, or the R bound to the ring nitrogen and T together are a radical of the formula

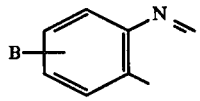

and B, the other R and Y have the stated meanings, may be manufactured by reacting compounds of the formula Y—COCH₂COO—alkyl with compounds of the formula

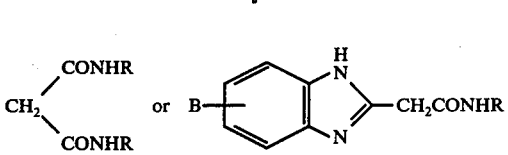

Suitable reaction conditions are similar to those for the manufacture of, for example, 2-hydroxy-3-cyano-6-pyridones.

The reactions are known in principle. Details may be found in the Examples, in which parts and percentages are by weight.

The invention in particular relates to compounds of the formula I, where A is a radical of the formula

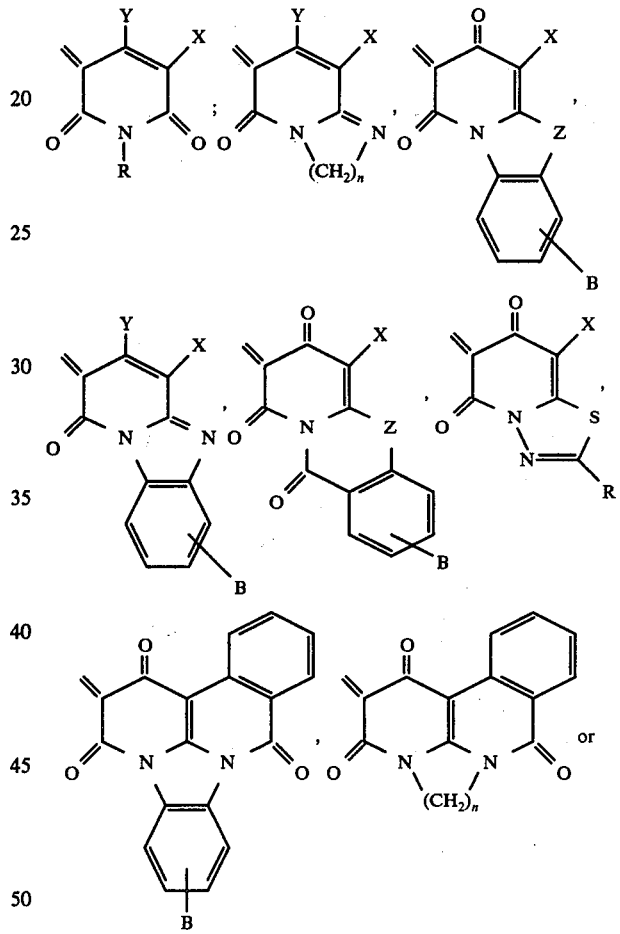

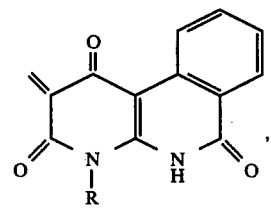

n is 2 or 3, R is hydrogen, alkyl of 1 to 12 carbon atoms, hydroxyalkyl of 2 or 3 carbon atoms, alkoxyalkyl of 3 to 8 carbon atoms, β-chloroethyl, β-cyanoethyl, alkoxycarbonylethyl, where alkoxy is of 1 to 4 carbon atoms, carbamoylethyl, N-mono- or N-di-alkylcarbamoylethyl, where alkyl is of 1 to 4 carbon atoms, cyclohexyl, benzyl, phenylethyl or phenyl, R¹ is hydrogen, chlorine, bromine, methyl, ethyl, methoxy, ethoxy, nitro, phenylmercapto or phenylmercapto substituted by chlorine, methyl or methoxy, $R^2$ is hydrogen or chlorine, $R^3$ is hydrogen, chlorine, bromine, methyl, ethyl, methoxy, ethoxy, phenoxy and nitro, alkanoylamino of 1 to 4 carbon atoms, benzoylamino, alkylsulfonylamino of 1 to 4 carbon atoms, phenylsulfonylamino, tolylsulfonylamino, alkylmercapto of 1 to 4 carbon atoms, phenylmercapto which is unsubstituted or substituted by chlorine, methyl or methoxy, alkylsulfonyl of 1 to 4 carbon atoms, phenylsulfonyl, tolylsulfonyl, sulfamoyl which is unsubstituted or is monosubstituted or disubstituted by alkyl of 1 to 8 carbon atoms, hydroxyalkyl of 2 or 3 carbon atoms, alkoxyalkyl of a total of 3 to 11 carbon atoms, β-cyanoethyl, β-chloroethyl, cyclohexyl, phenylalkyl (where alkyl is of 1 to 4 carbon atoms) or phenyl, sulfopiperidide, sulfopyrrolidide, sulfomorpholide, alkanoyl of 1 to 4 carbon atoms, chloroacetyl, β-chloropropionyl, or benzoyl which is unsubstituted or substituted by chlorine, methyl or methoxy, $R^4$ is hydrogen, chlorine, methoxy, ethoxy, alkylmercapto of 1 to 4 carbon atoms or phenylmercapto which is unsubstituted or substituted by chlorine, methyl or methoxy, $R^3$ and $R^4$ together are a radical of the formula

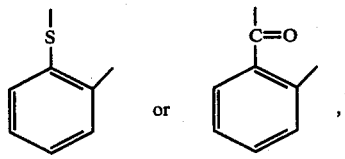

$R^5$ is hydrogen, chlorine, methoxy or ethoxy, B is hydrogen, methyl, methoxy or chlorine, X is cyano, carbamoyl or CONHR, Y is hydrogen, hydroxyl, alkyl of 1 to 4 carbon atoms, chlorine, bromine, alkoxycarbonyl (where alkoxy is of 1 to 4 carbon atoms) or CONHR, or X and Y together are a radical of the formula

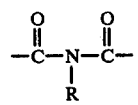

and Z is $\diagdown$N—R or —S—.

Dyes which are industrially particularly important are those of the formula I a

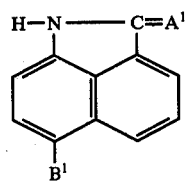

where $B^1$ is hydrogen, alkylsulfonyl of 1 to 4 carbon atoms, allylsulfonyl, propargylsulfonyl, alkanoyl of 2 to 8 carbon atoms, benzoyl, alkylmercapto of 1 to 4 atoms or phenylmercapto, $A^1$ is a radical of the formula

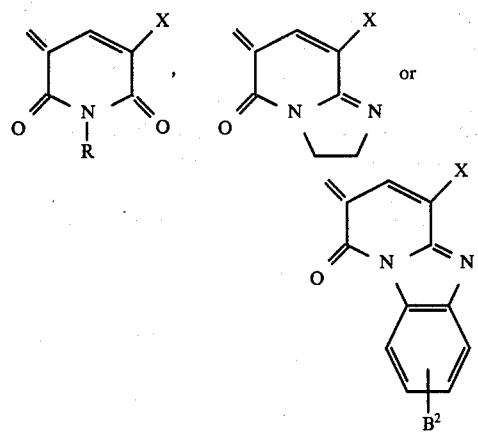

$B^2$ is hydrogen or methyl, and R and X have the stated meanings.

Specific examples of radicals $B^1$, in addition to those already mentioned, are methylsulfonyl, ethylsulfonyl, propylsulfonyl and butylsulfonyl, acetyl, propionyl, butyryl, hexanoyl, β-ethylhexanoyl and methylmercapto, ethylmercapto, propylmercapto and butylmercapto.

X is preferably cyano.

Examples of preferred radicals R are methyl, ethyl, n-propyl and i-propyl, n-butyl and i-butyl, ω-hydroxyethyl and ω-hydroxypropyl, and ω-alkoxyethyl and ω-alkoxypropyl, where alkoxy is of 1 to 4 carbon atoms.

The compounds of the formula I may be used as dyes for textile material, especially made of polyesters, and for coloring plastics, eg. polystyrene, polycarbonate, polyolefins, polyesters, polyacrylonitrile and nylons, so as to retain their transparency.

The new dyes give brilliant hues ranging from orange to blue, which have excellent fastness to light, thermofixation and wet treatments. The fact that some of the dyes are of very high tinctorial strength should also be singled out.

EXAMPLE 1

180 parts of phosphorus oxychloride are added dropwise, at 80° C, to a mixture of 1,500 parts of ethylene glycol dimethyl ether, 169 parts of naphtholactam and 170 parts of 1-ethyl-3-cyano-6-hydroxypyrid-2-one. After a short time, a red solution forms, from which red crystals begin to separate out. The mixture is stirred for 4 hours at 80° C and 1,000 parts of methanol are added whilst the mixture is cooling. After it has cooled, the product is filtered off, washed with methanol and dried. 267 parts of a dye of the structure

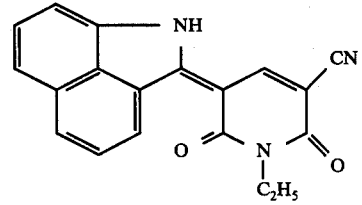

are obtained in the form of dark red crystals. When used to dye polyesters from an aqueous bath, the dye gives brilliant yellowish red hues having very good fastness properties.

Dyes with very similar hues are obtained if 1-ethyl-3-cyano-6-hydroxypyrid-2-one is replaced by the corresponding 1-propyl-, 1-butyl-, 1-(3-methoxypropyl)- or 1-(2-ethyl-hexyl)-compounds.

When 6-ethoxy-1,8-naphtholactam is condensed by a similar method with N-substituted 3-cyano-6-hydroxy-pyrid-2-ones, dyes which dye polyesters in neutral red hues are obtained; the dyeings are outstandingly fast.

EXAMPLE 2

276 parts of N-ethyl-4-bromonaphtholactam and 226 parts of 1-phenyl-3-cyano-4-methyl-6-hydroxypyrid-2-one are introduced into 1,000 parts of toluene and the mixture is stirred at 90° C. 165 parts of phosphorus oxychloride are added dropwise in the course of an hour and the mixture is stirred for a further 2 hours at 90° C. An equal volume of methanol is then added and the mixture is allowed to cool whilst stirring. After filtering off, washing with methanol and drying, 311 parts of a dye of the structure

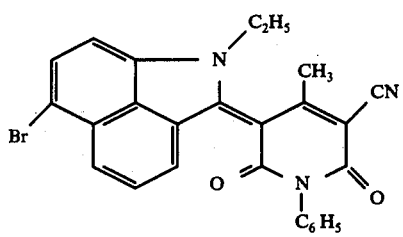

are obtained in the form of a dark crystal powder.

The dye may be used for mass-coloring polystyrene to give brilliant blue hues of good lightfastness and good heat stability.

Dyes having similar blue hues are obtained when N-ethyl-4-bromonaphtholactam is replaced by the corresponding N-butyl, N-methoxyethyl or N-cyclohexyl compounds.

EXAMPLE 3

The "naphthostyrol-imide chloride" obtained from 169 parts of naphtholactam by the method described in German Laid-Open Application DOS 1,445,624, and 209 parts of the benzimidazopyridone of the formula (B = H, Y = H)

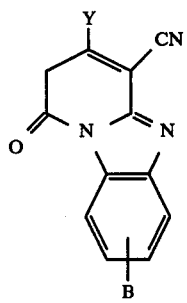

are introduced into 1,000 parts of nitrobenzene and the mixture is stirred at 85° C until the elimination of hydrogen chloride has ceased. After the mixture has cooled, the suspended crystals are filtered off, washed with ethanol and dried. 301 parts of a dye of the structure

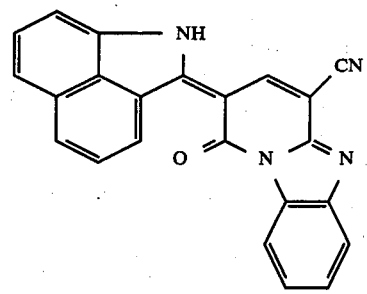

are obtained in the form of dark crystals. When used to dye polyesters from an aqueous bath, the dye gives violet dyeings which are outstandingly fast. Dyes with similar tinctorial properties are obtained if benzimidazopyridones substituted in the benz-nucleus (B = —CH$_3$, —OCH$_3$, —Cl, Y = H) are employed as the starting material. The analogous dye with Y = CH$_3$ and B = H is blue and may be used to color thermoplastics, giving fast blue hues.

EXAMPLE 4

385 parts of 2,4-bis-(phenylmercapto)-naphtholactam and 185 parts of 1-methyl-3-cyano-4-ethyl-6-hydroxy-pyrid-2-one are introduced into 1,000 parts of chlorobenzene and the mixture is stirred at 90° C. 165 parts of phosphorus oxychloride are added dropwise and stirring is continued for 1 hour at 90° C. 1,200 parts of methanol are now added to the reaction mixture, which is then left to stand for 24 hours. The product is then filtered off, washed with methanol and dried. 339 parts of a dye of the structure

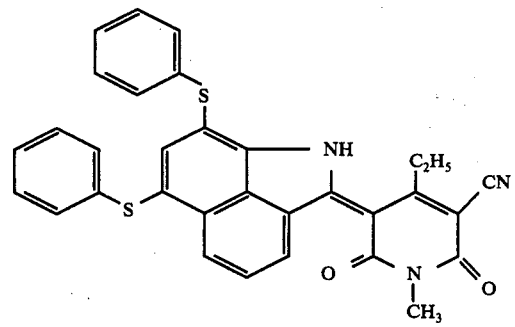

are obtained, which may be used for dyeing polyesters from an aqueous bath, and for mass-coloring polystyrene, giving pure reddish blue hues.

If 2,4-bis-(phenylmercapto)-naphtholactam is replaced by the corresponding 2,4-bis-(p-tolyl)- or 2,4-bis-(4-methoxyphenyl)- compounds, dyes giving neutral blue hues are obtained.

EXAMPLE 5

183 parts of naphtholactam-o-methyl ether and 250 parts of 1-(3-ethoxypropyl)-3-cyano-4,6-dihydroxypyrid-6-one are stirred into 1,200 parts of ethylene glycol and the mixture is heated to 125° C. It is then stirred for 8 hours at 125° – 130° C and the methanol formed is distilled off through a descending condenser. After the reaction mixture has cooled, it is filtered and the product is washed with ethanol and dried. 281 parts of a dye of the structure

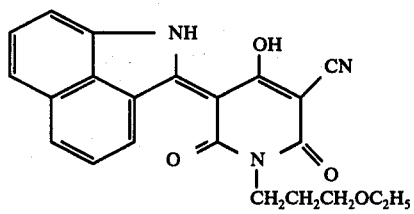

are obtained in the form of reddish brown crystals. The dye may be used for dyeing polyesters in orange red hues exhibiting a high level of fastness.

EXAMPLE 6

A mixture of 600 parts of butyrolactone, 277 parts of 4-phenylmercaptonaphtholactam and 155 parts of 1-methyl-3-cyano-6-hydroxypyrid-2-one is stirred at 80° C. 170 parts of phosphorus oxychloride are added dropwise and stirring is continued for 2 hours at 80° C. 1,000 parts of methanol are then added to the reaction mixture and the product is filtered off and rinsed with methanol. After drying, 299 parts of a dye of the structure

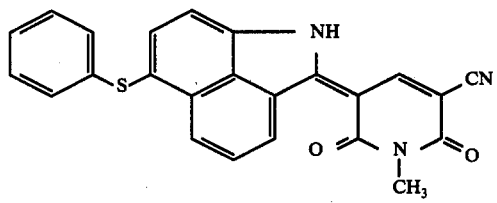

are obtained in the form of brown crystals. The dye may be used for dyeing polyesters from an aqueous bath, giving vivid violet hues; the dyeings have outstanding light fastness and fastness to thermofixation. Dyes of a similar hue are obtained if the phenylmercapto-naphtholactam is replaced by the corresponding 4-tolylmercapto-, 4-methoxyphenylmercapto-, 4-chlorophenylmercapto- or 4-carbomethoxyphenylmercapto-naphtholactam.

EXAMPLE 7

271 parts of 4,5-benzoylene-naphtholactam (prepared as described in CA 53, 9183 g) and 239 parts of benzimidazopyridone of the formula

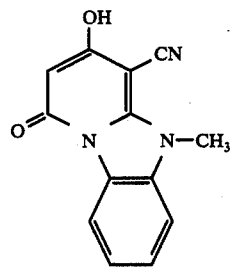

are introduced into 1,200 parts of butyrolactone and the mixture is stirred at 120° C. 200 parts of phosphorus oxychloride are added dropwise and stirring is continued for 6 hours at 120° C. The product is filtered off at 80° C and is rinsed with warm ethanol. After drying, 399 parts of the dye of the structure

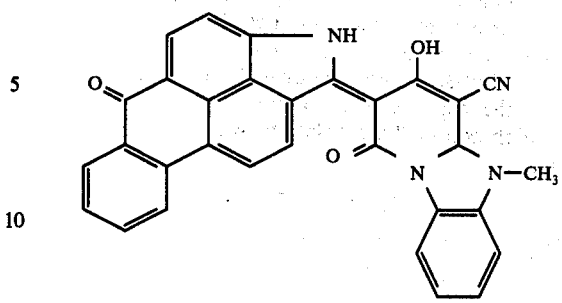

are obtained in the form of red crystals. When worked into thermoplastics, the dye gives brilliant red hues having very good lightfastness.

EXAMPLE 8

328 parts of N-benzyl-4,5-dichloro-1,8-naphtholactam and 150 parts of 1-methyl-3-cyano-6-hydroxyoyrid-2-one are introduced into 1,200 parts of butyrolactone and the mixture is stirred at 90° C. 190 parts of phosphorus oxychloride are then added dropwise whilst stirring and the mixture is kept at 90° C for 12 hours. It is diluted with 800 parts of ethanol and the product is filtered off and washed with ethanol. After drying, 413 parts of the dye of the structure

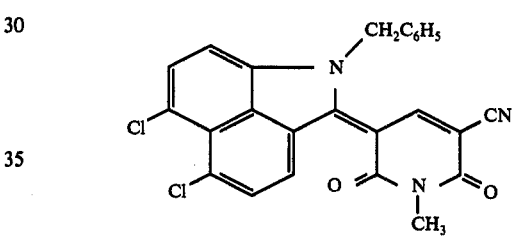

are obtained in the form of a dark crystal powder. The dye colors polystyrene in violet hues distinguished by very good lightfastness and heat stability. If 178 parts of 1-ethyl-3-cyano-4-methyl-6-hydroxypyrid-2-one are employed as the pyridone component, an analogous dye which may be used to color thermoplastics in blue hues is obtained.

EXAMPLE 9

307 parts of 3,4,5,6-tetrachloro-1,8-naphtholactam and 212 parts of 1-phenyl-3-cyano-6-hydroxypyrid-2-one are introduced into 1,500 parts of dehydrated nitrobenzene and the mixture is heated to 100° C. 300 parts of phosphorus oxychloride are added dropwise in the course of one hour and stirring is continued for 16 hours at 100° C. 500 parts of methanol are then added dropwise and the mixture is boiled for one hour under reflux. After filtering off, washing with methanol and drying, 443 parts of a dye of the structure

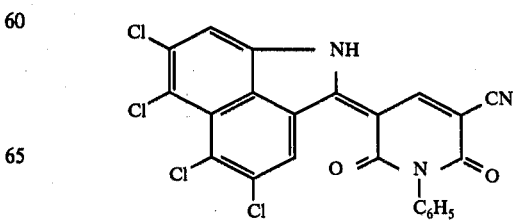

are obtained in the form of a dark red crystal powder. When worked into thermoplastics, the dye gives red hues having excellent lightfastness.

If N-ethyl-3,4,5,6-tetrachloro-1,8-naphtholactam is used as the naphtholactam component, an analogous dye which colors thermoplastics in fast violet hues is obtained.

EXAMPLE 10

275 parts of the compound

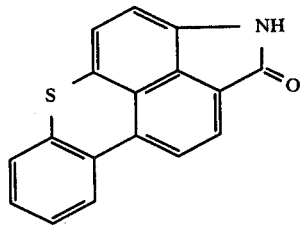

and 208 parts of 1-ethoxyethyl-3-cyano-6-hydroxypyrid-2-one are introduced into 2,000 parts of dichlorobenzene. The mixture is stirred at 90° C and 250 parts of phosphorus oxychloride are added in the course of 2 hours. Stirring is continued for 12 hours at 90° C and 1,000 parts of ethanol are then added carefully. The reaction mixture is boiled up briefly and is filtered warm. After washing the product with ethanol, and drying it, 398 parts of a dye of the structure

are obtained in the form of dark crystals having a metallic gloss. When worked into polystyrene, the dye gives fast greenish blue colorations.

The further dyes shown in the Table were obtained by the processes of Examples 1 – 10.

TABLE 1
Dyes

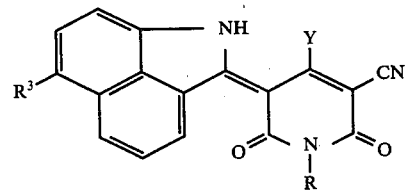

| Example | R | $R^3$ | Y | Hue |
|---|---|---|---|---|
| 11 | —(CH$_2$)$_3$OC$_5$H$_{11}$ | Cl | —CH$_3$ | violet |
| 12 | —(CH$_2$)$_2$COOC$_3$H$_7$ | H | —CH$_3$ | reddish violet |
| 13 | —⬡H | —OC$_2$H$_5$ | —CH$_3$ | violet |
| 14 | —CH$_2$C$_6$H$_5$ | —NHCOC$_2$H$_5$ | —CH$_3$ | violet |
| 15 | —CH$_3$ | —SC$_6$H$_5$ | —C$_2$H$_5$ | bluish violet |
| 16 | —CH$_2$CH$_2$OH | H | —C$_4$H$_9$ | violet |
| 17 | —C$_6$H$_5$ | —SC$_4$H$_9$ | —C$_4$H$_9$ | bluish violet |
| 18 | —H | —CH$_3$ | —Br | reddish violet |
| 19 | —CH$_3$ | H | H | yellowish red |
| 20 | —C$_2$H$_5$ | Br | H | red |
| 21 | —C$_2$H$_5$ | —NO$_2$ | H | reddish violet |
| 22 | —C$_2$H$_5$ | —OCH$_3$ | H | " |
| 23 | " | —NHCONHCH$_3$ | H | " |
| 24 | " | —NHSO$_2$C$_2$H$_5$ | H | " |
| 25 | " | —SCH$_3$ | H | bluish violet |
| 26 | " | —SCH$_2$CHOHCH$_3$ | H | " |
| 27 | " | —SO$_2$CH$_3$ | H | bluish red |
| 28 | " | —SO$_2$C$_6$H$_4$CH$_3$(4) | H | " |
| 29 | " | —COCH$_3$ | H | red |
| 30 | " | —COCH$_2$Cl | H | " |
| 31 | " | —COC$_6$H$_5$ | H | " |
| 32 | " | —SO$_2$N(C$_4$H$_9$)$_2$ | H | " |
| 33 | —C$_3$H$_7$(n) | H | H | yellowish red |
| 34 | " | —CH$_3$ | H | " |
| 35 | —C$_3$H$_7$(iso) | —NHCOCH$_3$ | H | reddish violet |
| 36 | —C$_4$H$_9$(n) | —NHSO$_2$C$_6$H$_4$CH$_3$(4) | H | " |
| 37 | —C$_4$H$_9$(n) | —SC$_2$H$_5$ | H | bluish violet |
| 38 | " | —COC$_6$H$_4$CH$_3$(4) | H | red |
| 39 | —CH$_2$CH$_2$OCH$_3$ | H | H | yellowish red |
| 40 | —CH$_2$CH$_2$OCH$_3$ | —SC$_6$H$_4$CH$_3$(4) | H | bluish violet |
| 41 | —(CH$_2$)$_3$OC$_2$H$_5$ | —SO$_2$N(CH$_3$)$_2$ | H | red |
| 42 | —(CH$_2$)$_3$OC$_4$H$_9$ | —NHCOC$_6$H$_5$ | H | reddish violet |
| 43 | —(CH$_2$)$_3$OC$_4$H$_9$ | —NHCOC$_6$H$_4$OCH$_3$(4) | H | " |
| 44 | —CH$_2$CH(C$_2$H$_5$)C$_4$H$_9$ | Br | H | red |
| 45 | —CH$_2$CH$_2$CN | (naphthyl) | H | bluish violet |
| 46 | —CH$_2$CH$_2$COOCH$_3$ | —NHCOC$_6$H$_4$OCH$_3$(4) | H | reddish violet |
| 47 | —CH$_2$CH$_2$COOC$_4$H$_9$ | H | H | yellowish red |
| 48 | —CH$_2$CH$_2$CONHC$_2$H$_5$ | —SO$_2$C$_2$H$_5$ | H | bluish red |

TABLE 1-continued

Dyes

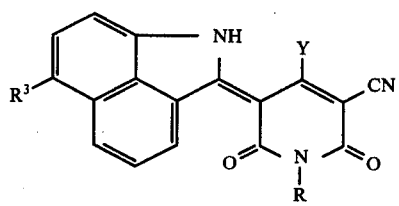

| Example | R | R³ | Y | Hue |
|---|---|---|---|---|
| 49 | —CH₂CH₂CON(CH₃)₂ | —SO₂C₆H₄Cl(4) | H | " |
| 50 | —CH₂CH₂CON(C₄H₉)₂ | H | H | yellowish red |
| 51 | —CH₂CH₂C₆H₅ | H | H | " |
| 52 | " | —SO₂N⟨pyrrolidine⟩ | H | red |
| 53 | —C₆H₅ | —SCH₂CH₂OH | H | bluish violet |
| 54 | " | —SC₆H₄OCH₃(4) | H | " |
| 55 | " | —SC₆H₄Cl(4) | H | " |
| 56 | " | —SO₂NHC₄H₉ | H | red |
| 57 | —C₆H₅ | —SO₂N(CH₃)(C₆H₅) | H | " |
| 58 | —CH₃ | —SC₆H₅ | OH | bluish red |
| 59 | —C₂H₅ | —COC₂H₅ | OH | reddish brown |
| 60 | " | —SO₂CH₃ | OH | red |
| 61 | " | —OC₂H₅ | OH | reddish brown |
| 62 | " | —NHSO₂CH₃ | OH | " |
| 63 | " | —SO₂N(C₃H₇)₂ | OH | red |
| 64 | —CH₂CH₂OC₂H₅ | —COC₆H₅ | OH | reddish brown |
| 65 | —(CH₂)₃OCH₃ | H | OH | orange |
| 66 | —(CH₂)₃OCH₃ | —SC₆H₄OC₆H₅ | OH | bluish red |
| 67 | —C₃H₇ | H | OH | orange |
| 68 | " | —SO₂CH₃ | OH | red |
| 69 | " | —SO₂C₆H₅ | OH | " |
| 70 | —CH₃ | H | —COOCH₃ | violet |
| 71 | " | —NHCONHC₆H₅ | —COOC₂H₅ | bluish violet |
| 72 | " | —COC₄H₉ | —COOC₂H₅ | violet |
| 73 | " | —NHSO₂CH₃ | —COOC₂H₅ | " |
| 74 | " | —SO₂NHCH₃ | —COOC₄H₉ | bluish violet |
| 75 | " | —SO₂NHC₆H₄CH₃(2) | —COOC₄H₉ | " |
| 76 | " | —SO₂N(C₂H₅)₂ | —CONHC₂H₅ | " |
| 77 | —C₂H₅ | H | —CONHC₂H₅ | violet |
| 78 | —CH₃ | Cl | —CON(CH₃)₂ | " |
| 79 | —C₄H₉ | H | —CON(CH₃)₂ | " |
| 80 | —CH₃ | —SC₆H₅ | —CON(C₂H₅)₂ | blue |
| 81 | " | —COC₆H₅ | —CON(C₃H₇)₂ | violet |

TABLE 2

Dyes

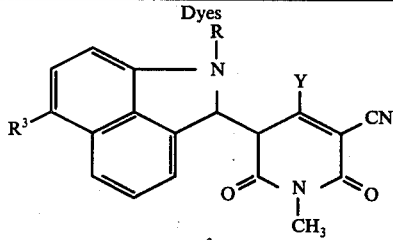

| Ex. | R | R³ | Y | Hue |
|---|---|---|---|---|
| 82 | —CH₃ | H | H | violet |
| 83 | —CH₃ | —SO₂CH₃ | H | bluish violet |
| 84 | —CH₃ | —SC₆H₅ | H | blue |
| 85 | —CH₂CH₂COOC₂H₅ | Cl | H | violet |
| 86 | —CH₂CH₂CN | Br | H | " |
| 87 | —CH₂CH₂CON(CH₃)₂ | H | H | " |
| 88 | —CH₂C₆H₅ | —SC₆H₃Cl₂(2,5) | H | blue |
| 89 | —C₆H₅ | —SCH₃ | H | " |
| 90 | —CH₃ | H | OH | violet |
| 91 | —CH₃ | H | CH₃ | blue |
| 92 | —CH₃ | Br | CH₃ | blue |

TABLE 2-continued

Dyes

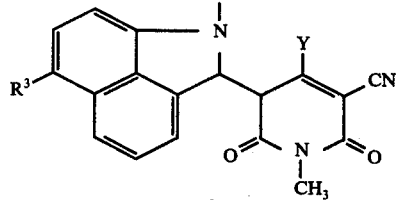

| Ex. | R | R³ | Y | Hue |
|---|---|---|---|---|
| 93 | " | —SC₆H₅ | " | greenish blue |
| 94 | " | —SO₂C₆H₅ | " | blue |
| 95 | —C₂H₅ | —SCH₃ | " | turquoise blue |
| 96 | " | —SO₂CH₃ | " | " |
| 97 | —CH₂CH₂C₆H₅ | —COC₆H₅ | C₂H₅ | " |
| 98 | —CH₂CH₂COOCH₃ | H | C₂H₅ | " |
| 99 | " | Br | " | " |

TABLE 3

Dyes

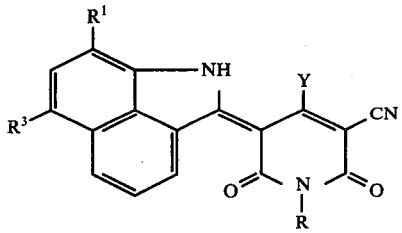

| Ex. | R | R¹ | R³ | Y | Hue |
|---|---|---|---|---|---|
| 100 | —CH₃ | —SC₂H₅ | —SC₂H₅ | —CH₃ | blue |
| 101 | " | —SC₆H₄CH₃(4) | —SC₆H₄CH₃(4) | —CH₃ | " |
| 102 | " | Cl | Cl | —C₂H₅ | reddish violet |
| 103 | " | Br | NO₂ | " | violet |
| 104 | " | —SC₆H₄Cl(4) | —SC₆H₄Cl(4) | " | blue |
| 105 | —C₂H₅ | Br | Br | —CH₃ | reddish violet |
| 106 | " | —SC₆H₅ | —SC₆H₅ | " | reddish blue |
| 107 | —CH₃ | Br | Br | H | red |
| 108 | " | —SCH₃ | —SCH₃ | H | bluish violet |
| 109 | —C₂H₅ | Br | NO₂ | H | bluish red |
| 110 | —C₂H₅ | —SC₄H₉ | —SC₄H₉ | H | bluish violet |
| 111 | " | —SC₆H₅ | —SC₆H₅ | H | bluish violet |
| 112 | " | —SC₆H₄CH₃(4) | —NO₂ | H | " |
| 113 | —C₃H₇ | Cl | Cl | H | red |
| 114 | —C₄H₉ | —SCH₂CH₂OH | —SCH₂CH₂OH | H | bluish violet |
| 115 | —C₄H₉ | —SC₆H₄OCH₃(4) | —SC₆H₄OCH₃(4) | H | " |
| 116 | —CH₂C₆H₅ | Cl | Cl | H | red |
| 117 | —CH₂C₆H₅ | —SC₆H₄Cl(4) | —SC₆H₄Cl(4) | H | bluish violet |
| 118 | —C₆H₅ | —SC₃H₇ | —SC₃H₇ | H | " |
| 119 | —C₆H₅ | —SC₆H₅ | —SC₆H₅ | H | " |
| 120 | " | —SC₆H₃Cl₂(2,5) | —SC₆H₃Cl₂(2,5) | H | " |
| 121 | " | —C₂H₅ | H | CH₃ | reddish violet |
| 122 | " | NO₂ | Br | CH₃ | violet |

TABLE 4

Dyes

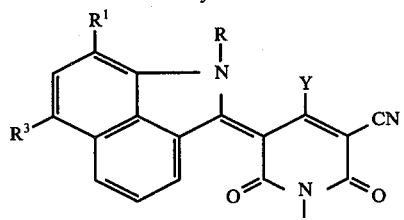

| Ex. | R | R¹ = R³ | Y | Hue |
|---|---|---|---|---|
| 123 | —CH₃ | Cl | —CH₃ | bluish violet |
| 124 | " | —SC₆H₅ | " | turquoise |
| 125 | —CH₂CH₂CON(C₂H₅)₂ | Br | " | bluish violet |
| 126 | —C₂H₅ | Cl | OH | violet |
| 127 | —CH₂CH₂C₆H₅ | Cl | —COOCH₃ | blue |
| 128 | —CH₂CH₂C₆H₅ | Br | " | blue |
| 129 | —CH₃ | Cl | H | violet |

TABLE 4-continued

Dyes

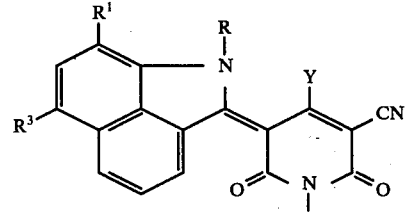

| Ex. | R | R¹ = R³ | Y | Hue |
|---|---|---|---|---|
| 130 | —C₂H₅ | —SC₂H₅ | H | blue |
| 131 | —C₂H₅ | —SC₄H₉ | H | " |
| 132 | —C₂H₅ | —SC₆H₅ | H | " |
| 133 | —CH₂CH₂OH | Br | H | violet |
| 134 | —(CH₂)₃OCH₃ | —SCH₃ | H | blue |
| 135 | —CH₂CH₂CN | " | H | " |
| 136 | —CH₂CH₂COOC₃H₇ | —SC₆H₅ | H | " |
| 137 | —CH₂CH₂CONHCH₃ | Cl | H | violet |
| 138 | —CH₂CH₂CON(C₃H₇)₂ | Br | H | " |
| 139 | —CH₂CH₂C₆H₅ | —SC₃H₇ | H | blue |

TABLE 5
Dyes

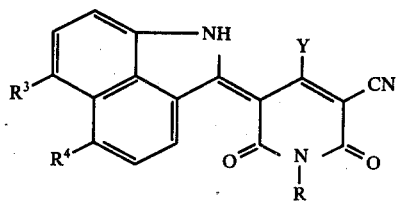

| Example | R | $R^3$ | $R^4$ | Y | Hue |
|---|---|---|---|---|---|
| 140 | H | Cl | Cl | H | red |
| 141 | H | —SCH$_3$ | —SCH$_3$ | H | bluish violet |
| 142 | —CH$_3$ | Cl | Cl | H | red |
| 143 | —C$_2$H$_5$ | Cl | —SC$_6$H$_5$ | H | violet |
| 144 | " | Cl | —SC$_6$H$_4$OCH$_3$(4) | H | " |
| 145 | " | Cl | —SC$_6$H$_4$Cl(4) | H | " |
| 146 | " | —SC$_2$H$_5$ | —SC$_2$H$_5$ | H | bluish violet |
| 147 | " | —SC$_6$H$_5$ | H | " | |
| 148 | —CH$_2$CH$_2$OH | Cl | Cl | H | red |
| 149 | —CH$_3$ | Cl | Cl | —CH$_3$ | reddish violet |
| 150 | —CH$_3$ | —SCH$_2$CH$_2$OH | —SCH$_2$CH$_2$OH | " | blue |
| 151 | —CH$_3$ | Cl | —SC$_6$H$_5$ | " | " |
| 152 | —CH$_3$ | H | OCH$_3$ | —CH$_3$ | reddish violet |

EXAMPLE 153

160 parts of phosphorus oxychloride are added dropwise at 70° C to a mixture of 800 parts of butyrolactone, 169 parts of naphtholactam and 188 parts of 1-ethyl-2-hydroxypyrid-6-one-3-carboxamide.

The mixture is stirred for 8 hours at 70° C, 400 parts of methanol and 400 parts of water are added successively and the whole is allowed to cool. After filtering off, washing and drying the product, 276 parts of the dye

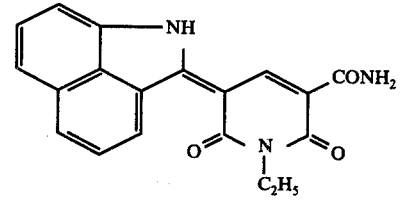

are obtained.

If the condensation is carried out at 70° C or with a substantial excess of phosphorus oxychloride, the reaction product contains substantial amounts of the dye described in Example 1. The dye of Example 153 is also obtained by hydrolyzing the dye 1, for example with 91% strength sulfuric acid at 85° C (more concentrated sulfuric acid leads to sulfonation of the naphthalene ring). The dye has very similar tinctorial properties to those of the dye described in Example 1.

TABLE 6
Dyes

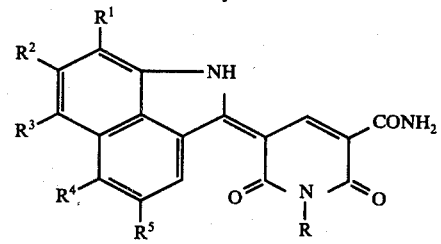

| Example | $R^1$ | $R^2$ | $R^3$ | $R^4$ | $R^5$ | R | Hue |
|---|---|---|---|---|---|---|---|
| 154 | H | H | H | H | H | —CH$_3$ | yellowish red |
| 155 | H | H | H | H | H | —(CH$_2$)$_3$OCH$_3$ | yellowish red |
| 156 | H | H | Cl | H | H | —C$_4$H$_9$ | red |
| 157 | H | H | Br | H | H | —C$_2$H$_5$ | red |
| 158 | Br | H | Br | H | H | —C$_2$H$_5$ | red |
| 159 | H | Cl | Cl | Cl | Cl | —C$_2$H$_5$ | red |
| 160 | H | H | —SC$_6$H$_5$ | H | H | —C$_2$H$_5$ | violet |
| 161 | H | H | —SC$_6$H$_5$ | —SC$_6$H$_5$ | H | —C$_2$H$_5$ | violet |
| 162 | H | H | —COC$_6$H$_5$ | H | H | —C$_2$H$_5$ | red |
| 163 | H | H | —COCH$_2$CH$_2$Cl | H | H | —CH$_3$ | red |
| 164 | H | H | —SO$_2$CH$_3$ | H | H | —C$_2$H$_5$ | bluish red |
| 165 | H | H | —NO$_2$ | H | H | —C$_2$H$_5$ | reddishviolet |
| 166 | H | H | —SO$_2$NHCH$_2$CH(C$_2$H$_5$)C$_4$H$_9$ | H | H | —C$_2$H$_5$ | red |

TABLE 6-continued

Dyes

[Structure shown with R¹, R², R³, R⁴, R⁵ substituents on naphtholactam-NH with CONH₂ group and N-R]

| Example | R¹ | R² | R³ | R⁴ | R⁵ | R | Hue |
|---|---|---|---|---|---|---|---|
| 167 | H | H | —SO₂N(CH₃)₂ | H | H | —C₂H₅ | red |
| 168 | —SC₆H₅ | H | —SC₆H₅ | H | H | —C₂H₅ | bluish violet |
| 169 | —S—C₆H₄—CH₃ | H | —S—C₆H₄—CH₃ | H | H | —C₂H₅ | bluish violet |
| 170 | H | H | —SO₂N(C₃H₇)₂ | H | H | —C₂H₅ | red |
| 171 | H | H | —SO₂N(piperidinyl) | H | H | —C₂H₅ | red |
| 172 | H | H | —SO₂NH—C₆H₁₁ | H | H | —C₂H₅ | red |
| 173 | H | H | —SO₂NH—C₆H₅ | H | H | —C₂H₅ | red |
| 174 | H | H | —SO₂N(CH₃)(C₆H₅) | H | H | —C₂H₅ | red |

EXAMPLE 175

200 parts of phosphorus oxychloride are added dropwise, at 80° C, to a mixture of 1,200 parts of ethylene glycol dimethyl ether, 247 parts of 4-methylsulfonyl-naphtholactam and 264 parts of N,N'-dipropyl-2-hydroxypyrid-6-one-3,4-dicarboximide. Dark crystals separate out from the solution. The mixture is boiled for 2 hours under reflux and 800 parts of methanol are added whilst it is cooling. After it has cooled, the product is filtered off, washed with methanol and dried. 401 parts of the dye having the structure

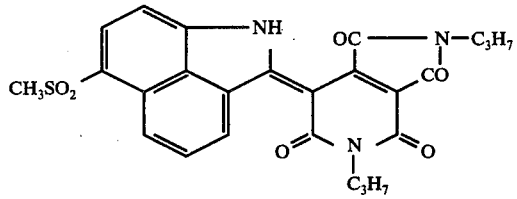

are obtained in the form of dark crystals having a metallic gloss. The dye may be used to dye polyesters, from an aqueous bath, in brilliant neutral blue hues having good fastness properties.

TABLE 7

Dyes

[Structure shown with R¹, R², R³, R⁴, R⁵ substituents and N-R group]

| Example | R¹ | R² | R³ | R⁴ | R⁵ | R | Hue |
|---|---|---|---|---|---|---|---|
| 176 | H | H | H | H | H | —CH₂CH(C₂H₅)(C₄H₉) | violet |
| 177 | H | H | H | H | H | —CH₂CH₂C₆H₅ | bluish violet |
| 178 | Cl | H | Cl | H | H | —C₄H₉(iso) | reddish blue |
| 179 | Cl | H | Cl | Cl | Cl | —CH₂CH₂CN | reddish blue |
| 180 | H | H | Br | H | H | —(CH₂)₃OCH₃ | bluish violet |

TABLE 7-continued
Dyes

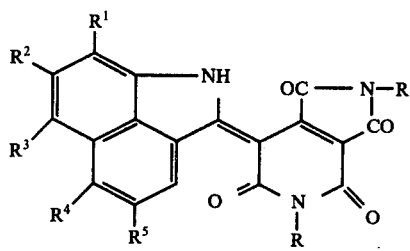

| Example | R¹ | R² | R³ | R⁴ | R⁵ | R | Hue |
|---|---|---|---|---|---|---|---|
| 181 | H | H | Br | H | H | cyclohexyl (—C₆H₁₁) | bluish violet |
| 182 | H | H | H | H | H | —C₆H₅ | reddish blue |
| 182 | H | H | C₂H₅SO₂— | H | H | —C₂H₅ | blue |
| 183 | H | H | CH₃C₆H₄SO₂— | H | H | —C₄H₉ | blue |
| 184 | H | H | CH₃CO | H | H | —C₅H₁₁ | reddish blue |
| 185 | H | H | ClCH₂CO | H | H | —C₃H₇(iso) | reddish blue |
| 186 | H | H | C₂H₅CO | H | H | —C₂H₅ | reddish blue |
| 187 | H | H | 2-Cl-C₆H₄-CO— | H | H | —C₂H₅ | reddish blue |
| 188 | H | H | 3-Cl-C₆H₄-CO— | H | H | —C₂H₅ | reddish blue |
| 189 | H | H | 4-CH₃-C₆H₄-CO— | H | H | —C₂H₅ | reddish blue |
| 190 | H | H | (C₂H₅)(C₄H₉)CH—CH₂NHSO₂— | H | H | —C₂H₄ | bluish violet |
| 192 | H | H | (CH₃)(C₆H₅)NSO₂— | H | H | —C₂H₅ | bluish violet |
| 193 | H | H | 3-F₃C-C₆H₄-NHSO₂— | H | H | —C₂H₅ | bluish violet |
| 194 | H | H | morpholino-NSO₂— | H | H | —C₂H₅ | bluish violet |
| 195 | H | H | CH₃NHCONH— | H | H | —C₂H₅ | bluish violet |
| 196 | H | H | NO₂ | H | H | —C₃H₇ | blue |

EXAMPLE 197

169 parts of naphtholactam and 227 parts of

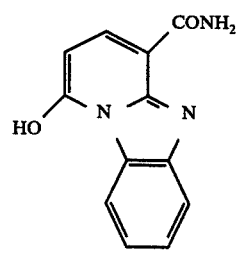

are introduced into 1,200 parts of dimethyl glycol and the mixture is stirred at 70° C. 165 parts of phosphorus oxychloride are added dropwise in the course of one hour and stirring is continued for 8 hours. After the mixture has cooled, it is filtered and the filter cake is dispersed in dilute ammonia. After again filtering off, and washing the product with water and drying it, 287 parts of the dye having the structure.

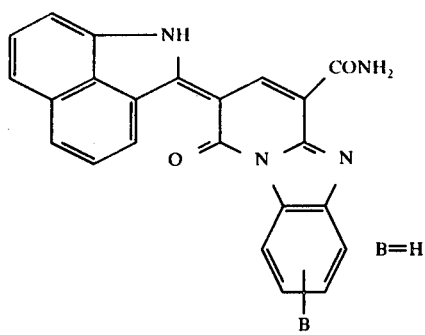

are obtained; it may be used to dye polyesters, from an aqueous bath, in light-fast violet hues. Dyes with B = $CH_3$ or $OCH_3$, which have been prepared similarly, exhibit a hue somewhat shifted toward blue.

TABLE 8

| Dyes | | | | |
|---|---|---|---|---|
| Ex. | R | $R^3$ | B | Hue |
| 198 | H | Br | H | violet |
| 199 | H | —$OCH_3$ | H | bluish violet |
| 200 | H | —$CH_3$ | H | violet |
| 201 | H | —$NO_2$ | H | bluish violet |
| 202 | H | —$SC_6H_5$ | H | blue |
| 203 | H | —$SC_6H_4CH_3(4')$ | H | blue |
| 204 | H | —$SC_6H_4OCH_3(4')$ | H | blue |
| 205 | —$CH_3$ | H | H | blue |
| 206 | —$CH_2CH_2CN$ | H | H | blue |
| 207 | —$CH_2CH_2COOC_2H_5$ | H | H | blue |
| 208 | H | Cl | $OCH_3$ | blue |
| 209 | H | H | Cl | violet |

EXAMPLE 210

169 parts of naphtholactam and 309 parts of a compound having the structure.

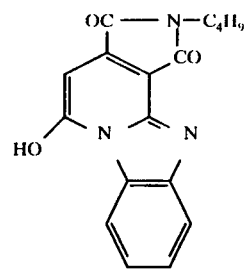

are introduced into 1,500 parts of ethylene glycol dimethyl ether, and 185 parts of phosphorus oxychloride are added at 75° C. After boiling the mixture for 4 hours, 500 parts of ethanol are added dropwise and the batch is allowed to cool. 500 parts of water are then added dropwise and the product is filtered off and washed with dilute ammonia solution and with water. After drying, 344 parts of the dye having the structure

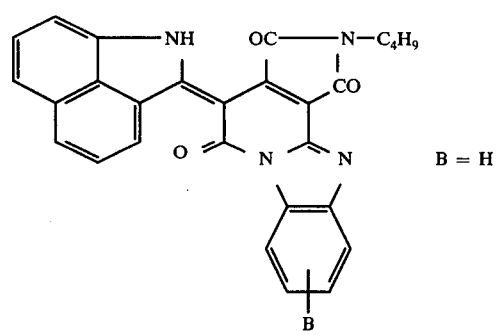

are obtained. This dye may be used to dye polyesters from an aqueous bath, giving slightly greenish blue dyeings with good fastness properties. Dyes of the same hue are obtained if the butyl group is replaced by other alkyl radicals, including substituted or branched radicals. Dues with B = $CH_3$ or $OCH_3$ exhibit a hue shifted somewhat more toward green.

The following are further dyes which have been prepared in accordance with the methods of Examples 1 - 10:

EXAMPLE 211

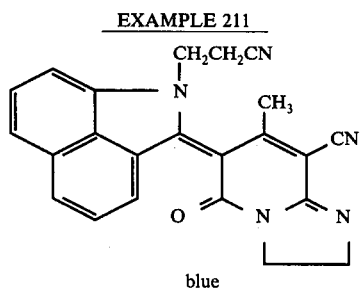

EXAMPLE 212

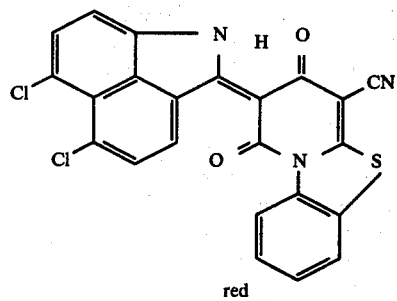
red

EXAMPLE 213

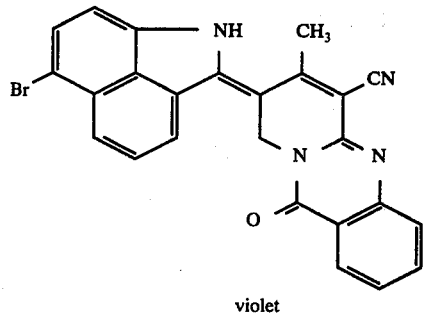
violet

EXAMPLE 214

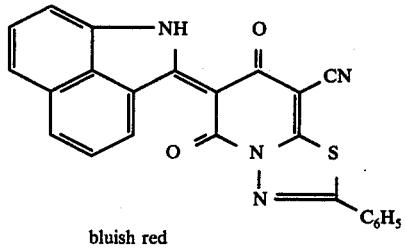
bluish red

EXAMPLE 215

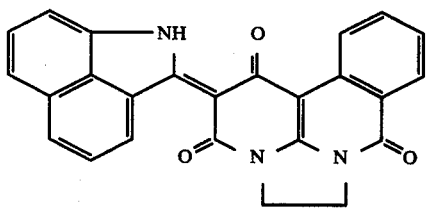
reddish violet

EXAMPLE 216

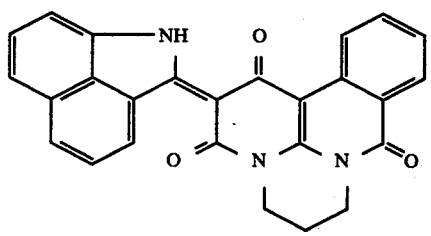
reddish violet

EXAMPLE 217

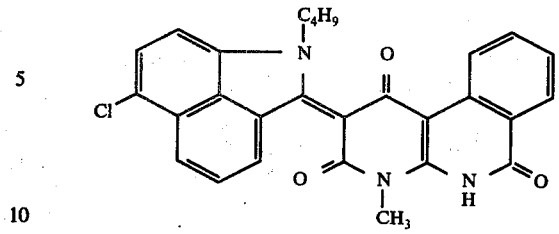
blue

EXAMPLE 218

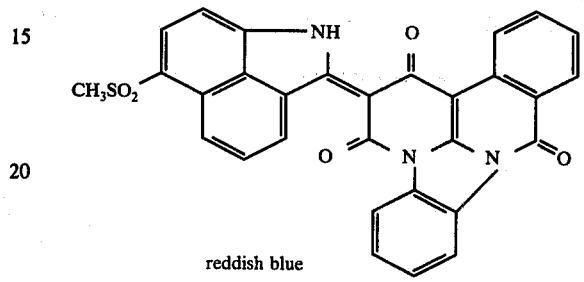
reddish blue

EXAMPLE 219

169 parts of naphtholactam and 210 parts of N,N'-diethyl2-hydroxypyrid-6-one-3-carboxamide are introduced into 750 parts of butyrolactone and the mixture is stirred at 70° C. 175 parts of phosphorus oxychloride are added dropwise, whereupon the reaction mixture assumes a deep red color. The mixture is stirred for a further 6 hours at 70° C, after which 250 parts of methanol and 250 parts of water are successively added dropwise. After the mixture was cooled, the crystals are filtered off and washed with 50% strength methanol. After drying, 309 parts of the dye having the structure

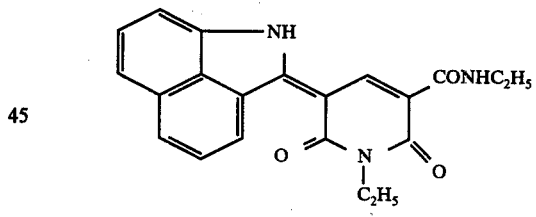

are obtained in the form of a red crystal powder. The dye may be used to dye polyester fibers and fabrics, from an aqueous bath, in brilliant red hues having very good fastness properties, especially excellent light fastness.

EXAMPLE 220

277 parts of 4-phenylmercaptonaphtholactam and 182 parts of N,N'-dimethyl-2-hydroxypyrid-6-one-3-carboxamide are introduced into 1,000 parts of dehydrated chlorobenzene. 180 parts of phosphorus oxychloride are added dropwise at 80° C, whilst stirring, and the mixture is then kept for 4 hours at 80° C. The heating bath is then temporarily removed and 1,000 parts of methanol are carefully added to the reaction mixture. The batch is then boiled for half an hour under reflux and is allowed to cool, and the product is filtered off.

After drying, 336 parts of the dye having the structure

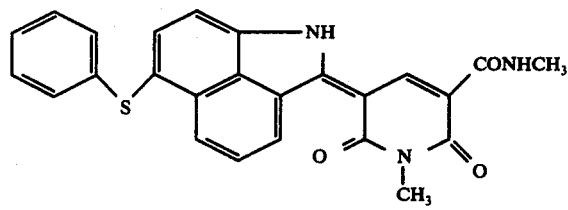

are obtained in the form of a dark crystal powder. The dye may be used to dye polyesters from an aqueous bath, giving light-fast violet hues.

The pyridone derivative is obtained as follows:

72 parts of sodium methylate are introduced into a mixture of 75 parts of ethyl formate and 120 parts of ethyl acetate at −10° to 0° C, whilst stirring. The mixture is left to stand overnight at room temperature, the colorless crystal slurry is then dissolved by pouring 750 parts by volume of absolute ethanol over it, and 130 parts of malonic acid bis-methylamide are introduced. The reaction mixture is now boiled for 8 hours under reflux, in the course of which it gradually solidfies to a crystal slurry. Excess 10% strength hydrochloric acid is then added and ethanol/water is distilled off until the internal temperature has reached 100° C. On cooling, colorless crystals separate out from the clear solution; they are filtered off and dried. Yield: 123 parts of 1-methyl-2-hydroxypyrid6-one-3-carboxylic acid methylamide of melting point 206° − 208° C.

Analysis: $C_8H_{10}N_2O_3$ (182) calculated C 52.8; H 5.5; N 15.4; O 26.4; found 52.8; 5.5; 15.5; 26.4.

TABLE 9

Dyes

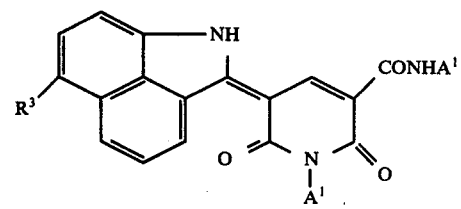

| Example | $R^3$ | $A^1$ | Hue |
|---|---|---|---|
| 221 | H | —CH$_3$ | red |
| 222 | H | —C$_3$H$_7$(n) | red |
| 223 | H | —C$_3$H$_7$(iso) | red |
| 224 | H | —C$_4$H$_9$(n) | red |
| 225 | H | —C$_4$H$_9$(sec) | red |
| 226 | H | —CH$_2$CH(C$_2$H$_5$)(C$_4$H$_9$) | |
| 227 | H | —CH$_2$CH$_2$OH | red |
| 228 | H | —CH$_2$CH$_2$OCOCH$_3$ | red |
| 229 | H | —CH$_2$CH$_2$OCOC$_6$H$_5$ | red |
| 230 | H | —CH$_2$CH$_2$CN | red |
| 231 | H | —CH$_2$CH$_2$CH$_2$OCH$_3$ | red |
| 232 | H | —CH$_2$CH$_2$CH$_2$OC$_3$H$_7$ | red |
| 233 | H | —CH$_2$C$_6$H$_5$ | red |
| 234 | H | —CH$_2$CH$_2$C$_6$H$_5$ | red |
| 235 | H | —CH$_2$CH$_2$CH$_2$OC$_6$H$_5$ | red |
| 236 | H | —cyclohexyl (H) | red |
| 237 | H | —CH$_2$CH(C$_6$H$_5$)CH$_3$ | red |
| 238 | H | —C$_6$H$_5$ | red |
| 239 | H | —C$_6$H$_4$Cl (o) | red |
| 240 | H | —C$_6$H$_4$CH$_3$ (p) | red |
| 241 | H | —C$_6$H$_4$OCH$_3$ (p) | bluish red |
| 242 | Cl | —C$_2$H$_5$ | red |
| 243 | Br | —C$_2$H$_5$ | bluish red |
| 244 | Br | —C$_3$H$_7$(iso) | bluish red |
| 245 | Br | —C$_4$H$_9$(n) | bluish red |
| 246 | —CH$_3$ | —CH$_3$ | red |
| 247 | —OC$_2$H$_5$ | —CH$_3$ | bluish red |
| 248 | —COCH$_3$ | —C$_2$H$_5$ | red |
| 249 | —COCH$_3$ | —C$_3$H$_7$ | red |
| 250 | —COC$_2$H$_5$ | —C$_2$H$_5$ | red |

TABLE 9-continued
Dyes

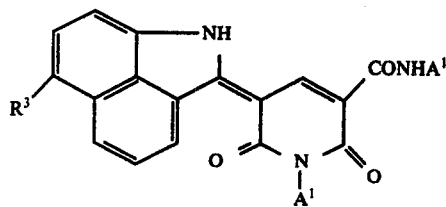

| Example | R³ | A¹ | Hue |
|---|---|---|---|
| 251 | —COCH₂Cl | —C₂H₅ | red |
| 252 | —COCH₂CH₂Cl | —C₂H₅ | red |
| 253 | —COC₆H₅ | —CH₃ | red |
| 254 | —COC₆H₅ | —C₃H₇ | red |
| 255 | —COC₆H₅ | —C₄H₉(sec) | red |
| 256 | —CO—C₆H₄(2-Cl) | —CH₃ | red |
| 257 | —CO—C₆H₄(3-Cl) | —CH₃ | red |
| 258 | —CO—C₆H₄(4-Cl) | —CH₃ | red |
| 259 | —CO—C₆H₄(4-CH₃) | —CH₃ | red |
| 260 | —CO—C₆H₄(3-CH₃) | —CH₃ | red |
| 261 | —SO₂CH₃ | —CH₃ | bluish red |
| 262 | —SO₂C₂H₅ | —CH₃ | bluish red |
| 263 | —SO₂CH₂CH=CH₂ | —CH₃ | bluish red |
| 264 | —SO₂NHC₂H₅ | —CH₃ | red |
| 265 | —SO₂NH(CH₂)₃OC₂H₅ | —CH₃ | red |
| 266 | —SO₂NHCH₂CH(C₂H₅)(C₄H₉) | —CH₃ | red |
| 267 | —SO₂NH(CH₂)₃OC₄H₉ | —C₂H₅ | red |
| 268 | —SO₂N(CH₃)₂ | —C₄H₉(n) | red |
| 269 | —SO₂N(CH(CH₃)₂)₂ | —CH₃ | red |
| 270 | —SO₂N(C₄H₉)₂ | —C₂H₅ | red |
| 271 | —SO₂NHC₆H₅ | —C₂H₅ | red |
| 272 | —SO₂N(CH₃)(C₆H₅) | —CH₃ | red |
| 273 | —SO₂NH—C₆H₄(3-CH₃) | —C₂H₅ | red |
| 274 | —SO₂NH—C₆H₁₁ | —C₃H₇(iso) | red |
| 275 | —SO₂NHCH₂C₆H₅ | —C₂H₅ | red |

TABLE 9-continued

Dyes

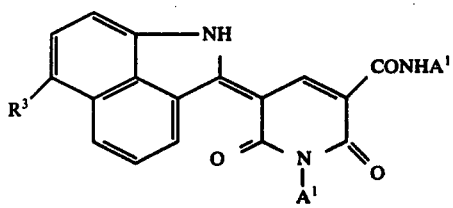

| Example | R³ | A¹ | Hue |
|---|---|---|---|
| 276 | —SO₂NH(CH₂)₃O(CH₂)₄OH | —CH₃ | red |
| 277 | —SO₂NH(CH₂)₃O(CH₃)₂OC₆H₅ | —CH₃ | red |
| 278 | —SO₂N⟨piperidine⟩ | —C₄H₉ | red |
| 279 | —SO₂N⟨piperidine⟩ | —C₄H₉(tertiary) | red |
| 280 | —SO₂N⟨piperidine⟩ | —C₃H₇(n) | red |
| 281 | —SO₂N⟨morpholine⟩ | —C₂H₅ | red |
| 282 | —SC₂H₅ | —CH₃ | violet |
| 283 | —SCH₂CH₂OH | —CH₃ | violet |
| 284 | —SC₄H₉ | —C₂H₅ | violet |
| 285 | —SC₆H₅ | —C₂H₅ | violet |
| 286 | —SC₆H₅ | —C₃H₇(iso) | violet |
| 287 | —S—C₆H₄—CH₃ | —CH₃ | violet |
| 288 | —S—C₆H₄—Cl | —CH₃ | violet |
| 289 | —S—C₆H₄—OCH₃ | —CH₃ | violet |
| 290 | —S—C₆H₄—OC₆H₅ | —CH₃ | violet |
| 291 | —S—C₆H₄—COOCH₃ | —CH₃ | violet |
| 292 | —S—naphthyl | —C₂H₅ | violet |
| 293 | —S—C₆H₄—NHCOCH₃ | —CH₃ | violet |
| 294 | —S—C₆H₄—CONHCH₃ | —CH₃ | violet |

TABLE 9-continued

Dyes

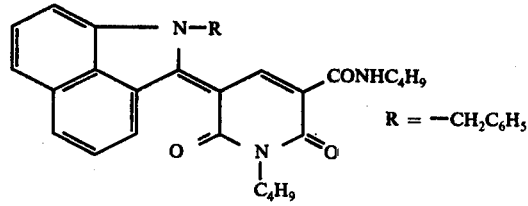

| Example | R³ | A¹ | Hue |
|---|---|---|---|
| 295 | —SO₂C₆H₅ | —C₂H₅ | bluish red |
| 296 | —SO₂—C₆H₄—CH₃ | —C₂H₅ | bluish red |
| 297 | —NO₂ | —CH₃ | bluish red |
| 298 | —NO₂ | —C₂H₅ | bluish red |
| 299 | —NO₂ | —C₃H₇ | bluish red |
| 300 | —NO₂ | —C₃H₇(iso) | bluish red |
| 301 | —NHCOCH₃ | —C₂H₅ | reddish violet |
| 302 | —NHCOC₂H₅ | —C₂H₅ | reddish violet |
| 303 | —NHCONH₂ | —C₂H₅ | reddish violet |
| 304 | —NHCOC₆H₅ | —C₃H₇ | reddish violet |
| 305 | —NHSO₂CH₃ | —C₂H₅ | reddish violet |
| 306 | —NHSO₂C₄H₉ | —CH₃ | reddish violet |
| 307 | —NHSO₂—C₆H₄—CH₃ | —C₂H₅ | reddish violet |
| 308 | —NHSO₂—C₆H₄—Cl | —C₂H₅ | reddish violet |

EXAMPLE 309

190 parts of phosphorus oxychloride are added in the course of one hour to a mixture of 1,200 parts of butyrolactone, 259 parts of N-benzyl-naphtholactam and 266 parts of N,N'-dibutyl-2-hydroxypyrid6-one-3-carboxamide at 100° C and the batch is kept at this temperature for 2 hours. The heating is then discontinued and 800 parts of methanol are added dropwise at a rate such that the reaction mixture comes to the boil. In the course thereof, the dark melt turns to a crystal suspension, which is filtered after it has cooled. After washing the product with methanol and drying, 355 parts of the dye having the structure

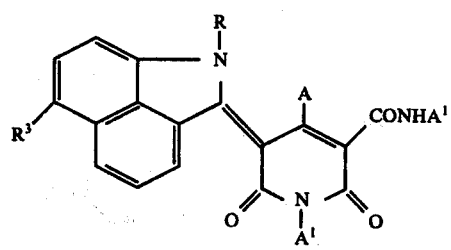

R = —CH₂C₆H₅ are obtained. When worked into thermoplastics, the dye gives violet hues having very good lightfastness. Tinctorially equivalent dyes are obtained with N-phenyl-naphtholactam and N-phenylethylnaphtholactam.

TABLE 10

Dyes

| Example | R | R³ | A | A¹ | Hue |
|---|---|---|---|---|---|
| 310 | —CH₃ | H | H | —C₂H₅ | violet |
| 311 | —CH₃ | H | —CH₃ | —CH₃ | blue |
| 312 | —C₂H₅ | Br | H | —CH₃ | violet |
| 313 | —CH₃ | H | —C₄H₉ | —CH₃ | blue |
| 314 | H | —COC₆H₅ | —CH₃ | —CH₃ | reddish violet |
| 315 | H | H | OH | —C₂H₅ | orange |
| 316 | H | —SO₂CH₃ | OH | —C₃H₇ | yellowish red |
| 317 | H | —SC₆H₅ | OH | —CH₃ | dull bluish red |

TABLE 10-continued

Dyes

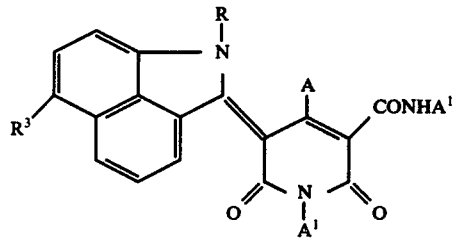

| Example | R | R³ | A | A¹ | Hue |
|---|---|---|---|---|---|
| 318 | H | —SO₂N(C₂H₅)₂ | OH | —C₂H₅ | yellowish red |
| 319 | —CH₂CH₂CN | H | OH | —CH₃ | violet |
| 320 | —C₄H₉ | —COC₆H₅ | OH | —C₂H₅ | violet |
| 321 | —C₂H₅ | —SC₆H₅ | OH | —CH₃ | reddish blue |
| 322 | —CH₂C₆H₅ | H | OH | —C₄H₉ | violet |
| 323 | —(CH₂)₂COOCH₃ | Cl | H | —C₂H₅ | violet |
| 324 | —(CH₂)₂CON(CH₃)₂ | H | H | —CH₃ | violet |
| 325 | —CH₃ | —SC₆H₅ | H | —CH₃ | reddish blue |
| 326 | —(CH₂)₃OCH₃ | Br | H | —CH₃ | violet |

TABLE 11

Dyes

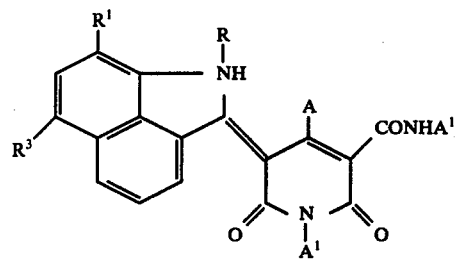

| Example | R¹ | R³ | A | A¹ | Hue |
|---|---|---|---|---|---|
| 327 | Cl | Cl | H | —C₂H₅ | red |
| 328 | Cl | NO₂ | H | —C₂H₅ | red |
| 329 | Br | Br | H | —C₃H₇ | bluish red |
| 330 | Br | NO₂ | H | —CH₃ | bluish red |
| 331 | NO₂ | Br | H | —C₂H₅ | red |
| 332 | —SCH₃ | —SCH₃ | H | —C₂H₅ | bluish violet |
| 333 | —SCH₂CH₂OH | —SCH₂CH₂OH | H | —CH₃ | bluish violet |
| 334 | —SC₆H₅ | —SC₆H₅ | H | —C₂H₅ | bluish violet |
| 335 | —S—⟨⟩—Cl | —S—⟨⟩—Cl | H | —CH₃ | violet |
| 336 | —S—⟨⟩—OCH₃ | —S—⟨⟩—OCH₃ | H | —C₂H₅ | bluish violet |
| 337 | Br | Br | OH | —C₂H₅ | reddish orange |
| 338 | —SC₆H₅ | —SC₆H₅ | OH | —CH₃ | violet |
| 339 | —S—⟨⟩—CH₃ | —S—⟨⟩—CH₃ | OH | —C₂H₅ | violet |
| 340 | Cl | Cl | —CH₃ | —CH₃ | reddish violet |
| 341 | —SC₆H₅ | —SC₆H₅ | —CH₃ | —CH₃ | blue |

TABLE 12

Dyes

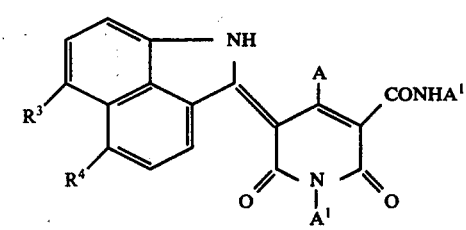

| Example | R³ | R⁴ | A | A¹ | Hue |
|---|---|---|---|---|---|
| 342 | Cl | Cl | H | —C₂H₅ | red |
| 343 | Cl | Cl | H | —C₃H₇ (iso) | red |
| 344 | —SC₂H₅ | —SC₂H₅ | H | —CH₃ | bluish violet |
| 345 | Cl | —SC₆H₅ | H | —C₂H₅ | reddish violet |

TABLE 12-continued

Dyes

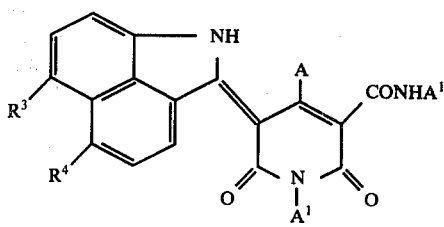

| Example | R³ | R⁴ | A | A¹ | Hue |
|---|---|---|---|---|---|
| 346 | Cl | —SC₆H₅ | H | —C₄H₉ | reddish violet |
| 347 | Cl | —S—⟨C₆H₄⟩—Cl | H | —C₂H₅ | reddish violet |
| 348 | Cl | —S—⟨C₆H₄⟩—CH₃ | H | —C₂H₅ | reddish violet |
| 349 | H | —OCH₃ | H | —CH₃ | red |
| 350 | Cl | Cl | OH | —C₂H₅ | orange |
| 351 | Cl | —S—⟨C₆H₄⟩—OCH₃ | OH | —C₂H₅ | red |
| 352 | —SC₆H₅ | —SC₆H₅ | OH | —C₂H₅ | reddish violet |
| 353 | Cl | Cl | —CH₃ | —CH₃ | reddish violet |
| 354 | —SCH₃ | —SCH₃ | —CH₃ | —C₂H₅ | blue |
| 355 | —S—⟨C₆H₄⟩—CH₃ | —S—⟨C₆H₄⟩—CH₃ | —CH₃ | —CH₃ | blue |

EXAMPLE 356

307 parts of 3,4,5,6-tetrachloronaphtholactam and 250 parts of N,N'-diisopropyl-2-hydroxypyrid-6-one are introduced into 1,300 parts of dehydrated nitrobenzene and the mixture is stirred at 90° C. 195 parts of phosphorus oxychloride are added dropwise and stirring is continued for 4 hours at 99° - 100° C. The excess phosphorus oxychloride is then decomposed by adding 700 parts of ethanol and the mixture is boiled up briefly and allowed to cool. After filtering off, washing the product with ethanol and drying it, 411 parts of the dye having the structure

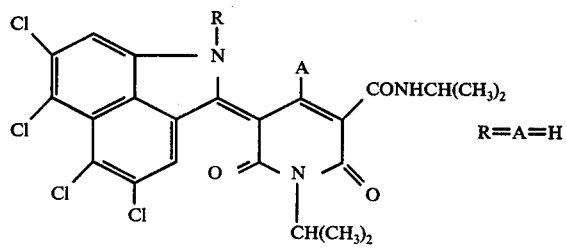

R=A=H are obtained. In polystyrene, this dye gives heat-stable and very light-fast brilliant red colorations. The dye with R = H and A = OH, prepared similarly, colors polystyrene reddish orange whilst the dye with R = —CH₃ and A = H colors polystyrene violet.

EXAMPLE 357

271 parts of 4,5-benzoylenenaphtholactam (prepared as described in C.A. 53, 9183 g) and 300 parts of N,N'-bis-methoxypropyl-2-hydroxypyrid-6-one-3-carboxamide are introduced into 1,200 parts of dehydrated dichlorobenzene and the mixture is stirred at 100° C. 200 parts of phosphorus oxychloride was added dropwise and stirring is continued for 4 hours at 110° C. When the mixture has cooled, 800 parts of methanol are added and the product is filtered off and washed with methanol. After it has been dried, 443 parts of the dye of the formula

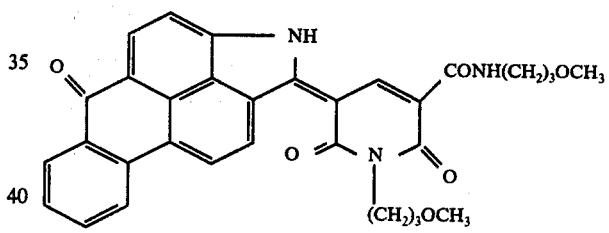

are obtained. When worked into thermoplastics, the dye gives reddish violet colorations distinguished by very good lightfastness.

EXAMPLE 358

275 parts of the compound

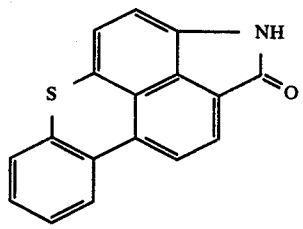

and 266 parts of N,N'-bis-isobutyl-2-hydroxypyrid-6-one-3-carboxamide are introduced into 1,500 parts of butyrolactone. The mixture is stirred at 90° C and 200 parts of phosphorus oxychloride are added in the course of 2 hours. Stirring is continued for 10 hours at 90° C and 1,000 parts of methanol are then added dropwise, whilst discontinuing the heating. After filtering off, washing the product with methanol and drying it, 336 parts of the dye having the structure

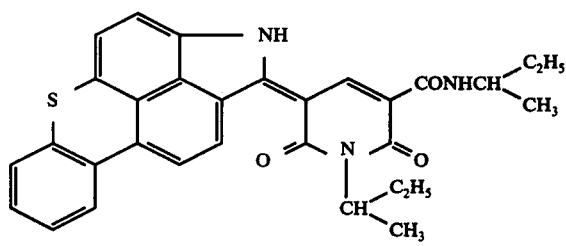

are obtained. This dye, worked into polystyrene or other thermoplastics, gives light-fast greenish blue colorations.

EXAMPLE 359

250 parts of phosphorus oxychloride are added in the course of 2 hours to a mixture of 1,400 parts of ethylene glycol dimethyl ether, 169 parts of naphtholactam and 299 parts of the compound

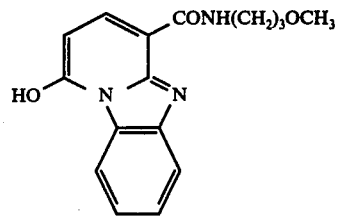

whilst stirring at 70° C. The mixture is then stirred for a further 6 hours at 70° C, after which 1,000 parts of methanol are added. When the mixture has cooled, it is filtered and the filter residue is dispersed in dilute ammonia. After again filtering off, washing the product with water and drying it, 297 parts of the dye

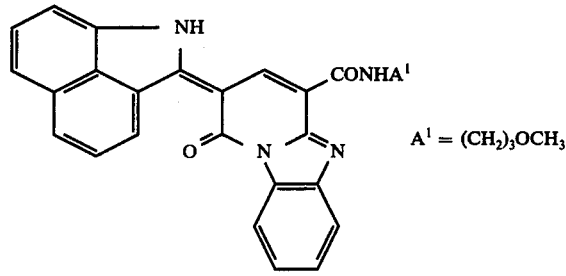

$A^1 = (CH_2)_3 OCH_3$ are obtained. This dye may be used to dye polyester fibers and fabrics from an aqueous bath, giving strong brilliant violet dyeings distinguished by good lightfastness and fastness to thermofixation. Dyes with equivalent tinctorial properties are obtained by varying $A^1$ from methyl to 2-ethylhexyl, the optimum affinity being found with a total of from 4 to 5 carbon atoms.

The condensation products may be prepared by, for example, the following method:

77 parts of sodium methylate are introduced into a mixture of 80 parts of ethyl formate and 140 parts of ethyl acetate whilst cooling at from −20° to 0° C. After being left to stand overnight, the colorless slurry of the sodium salt of formylethyl acetate is dissolved by adding 400 parts by volume of ethylene glycol monomethyl ether, and 189 parts of benzimidazolyl-2-aceto-N-methylamide are added to the solution. The mixture is boiled for 4 hours under reflux, 600 parts by volume of water are added and the batch is acidified with concentrated hydrochloric acid. The reaction mixture is boiled for ½ hour, sodium acetate is added until the mixture reacts neutral, and the product is filtered off. After washing the product with warm water and drying it, 208 parts of the compound of the formula

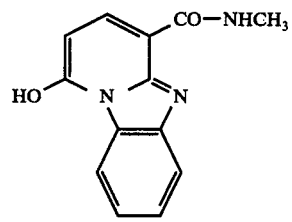

are obtained. The melting point of a sample recrystallized from dimethylformamide is 321° C (with decomposition).

Analysis: $C_{13}H_{11}N_3O_2$ (241); calculated C 64.8 H 4.6 N 17.4 O 13.3; found 64.5 4.9 17.3 13.7.

TABLE 13

Dyes

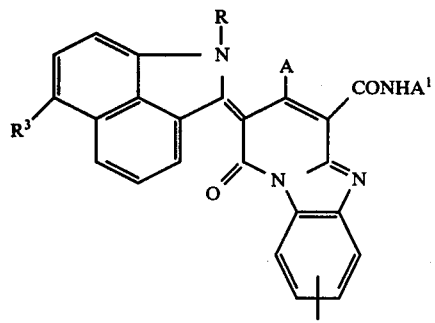

| Example | R | $R^3$ | A | $A^1$ | Y | Hue |
|---|---|---|---|---|---|---|
| 360 | —$C_2H_5$ | H | H | —$C_4H_9$ | H | blue |
| 361 | H | Br | H | —$C_2H_5$ | H | violet |

TABLE 13-continued

Dyes

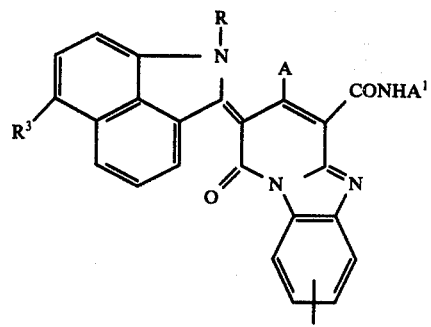

| Example | R | R³ | A | A¹ | Y | Hue |
|---|---|---|---|---|---|---|
| 362 | H | —SO₂CH₃ | H | —(CH₂)₃OC₂H₅ | H | bluish violet |
| 363 | H | H | H | —C₃H₇ | Cl | violet |
| 364 | H | H | H | —C₃H₇ | CH₃ | violet |
| 365 | H | Cl | H | —(CH₂)₃OCH₃ | —OCH₃ | bluish violet |
| 366 | H | —NO₂ | H | —(CH₂)₃OCH₃ | H | blue |
| 367 | H | —SC₆H₅ | H | —C₄H₉ | H | blue |
| 368 | H | —SO₂N(C₄H₉)₂ | H | —CH₃ | H | bluish violet |
| 369 | H | —SO₂NHCHCH₂ $\diagdown^{C_2H_5}_{C_4H_9}$ | H | —C₂H₅ | H | bluish violet |
| 370 | H | —COC₂H₅ | H | —C₄H₉ | H | bluish violet |
| 371 | H | H | —CH₃ | —CH₃ | H | blue |
| 372 | H | Br | —CH₃ | —CH₃ | H | blue |
| 373 | H | H | —OH | —C₂H₅ | H | reddish violet |
| 374 | —CH₃ | H | —OH | —CH₃ | H | bluish violet |
| 375 | —CH₂CH₂CN | Br | H | —CH₃ | H | blue |
| 376 | —CH₂C₆H₅ | H | H | —CH₃ | H | blue |
| 377 | H | H | H | —C₃H₇ | —CON(CH₃)₂ | bluish violet |
| 378 | H | Cl | H | —C₂H₅ | —CON(C₄H₉)₂ | bluish violet |
| 379 | H | H | H | —C₂H₅ | —COOCH₃ | bluish violet |

I claim:
1. A compound of the formula

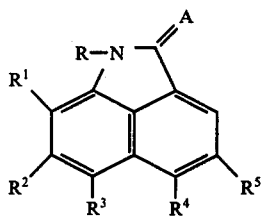

where A is

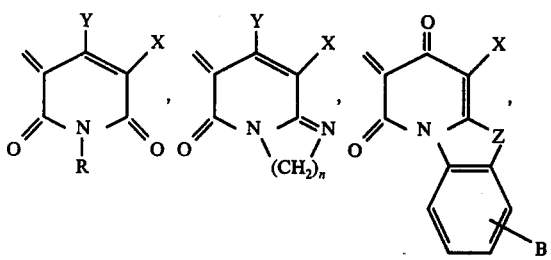

-continued

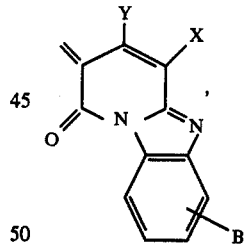

$n$ is 2, R is hydrogen, alkyl of 1 to 12 carbon atoms, hydroxyalkyl of 2 or 3 carbon atoms, alkoxyalkyl of 3 to 8 carbon atoms, β-chloroethyl, β-cyanoethyl, $C_1$ to $C_4$ alkoxycarbonylethyl, carbamoylethyl, N-mono- or N-di-alkylcarbamoylethyl, where alkyl is of 1 to 4 carbon atoms, cyclohexyl, benzyl, phenylethyl or phenyl, R¹ is hydrogen, chlorine, bromine, methyl, ethyl, methoxy, ethoxy, nitro and phenylmercapto, or phenylmercapto substituted by chlorine, methyl or methoxy, R² is hydrogen or chlorine, R³ is hydrogen, chlorine, bromine, methyl, ethyl, methoxy, ethoxy, phenoxy and nitro, alkanoylamino of 1 to 4 carbon atoms, benzoylamino, alkylsulfonylamino of 1 to 4 carbon atoms, phenylsulfonylamino, tolylsulfonylamino, alkylmercapto of 1 to 4 carbon atoms, phenylmercapto or phenylmercapto substituted by chlorine, methyl or methoxy, alkylsulfonyl of 1 to 4 carbon atoms, phenylsulfonyl, tolylsulfonyl, sulfamoyl which is unsubstituted or is monosubstituted or disubstituted by alkyl of 1 to 8 carbon atoms, hydroxyalkyl of 2 or 3 carbon atoms, alkoxyalkyl of a total of 3 to 11 carbon atoms, β-cyanoethyl, β-chloroethyl, cyclohexyl, phenylalkyl (where alkyl is of 1 to 4 carbon atoms) or phenyl, sulfopiperidide, sulfopyrrolidide, sulfomorpholide, alkanoyl of 1 to 4 carbon atoms, chloroacetyl, β-chloropropionyl, benzoyl or benzoyl substituted by chlorine, methyl or methoxy, $R^4$ is hydrogen, chlorine, methoxy, ethoxy, alkylmercapto of 1 to 4 carbon atoms or phenylmercapto or phenylmercapto substituted by chlorine, methyl or methoxy, $R^3$ and $R^4$ together are

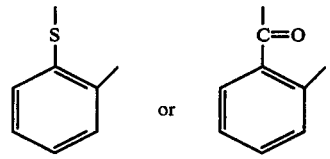

or $R^5$ is hydrogen, chlorine, methoxy or ethoxy, B is hydrogen, methyl, methoxy or chlorine, X is cyano, carbamoyl or CONHR, Y is hydrogen, hydroxyl, alkyl of 1 to 4 carbon atoms, chlorine, bromine, $C_1$ to $C_4$ alkoxycarbonyl or CONHR, or X and Y together are

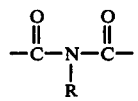

and Z is $\diagdown$N—R or —S—.

and Z is >N-R.

2. A compound as claimed in claim 1, where $R^2$, $R^4$ and $R^5$ are hydrogen.
3. A compound as claimed in claim 1, where $R^1$ is hydrogen, chlorine or bromine.
4. A compound as claimed in claim 1, where $R^3$ is hydrogen, chlorine, bromine, methoxy, ethoxy, phenylmercapto, benzoyl, phenylmercapto or benzoyl substituted by chlorine, methyl or methoxy, methylsulfonyl, acetyl, propionyl or sulfamoyl which is monosubstituted or disubstituted by alkyl of 4 to 8 carbon atoms.
5. A compound as claimed in claim 1, where R is hydrogen, alkyl of 1 to 8 carbon atoms, hydroxyalkyl of 2 or 3 carbon atoms, alkoxyalkyl of a total of 3 to 8 carbon atoms, or β-cyanoethyl.
6. A compound as claimed in claim 1, where A is

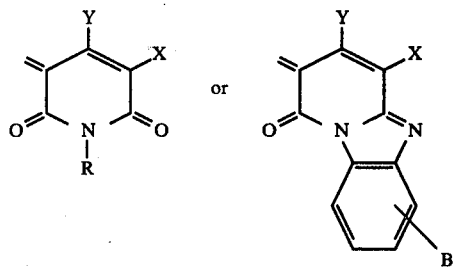

B is hydrogen, chlorine, methyl or methoxy, R is hydrogen, alkyl of 1 to 8 carbon atoms, hydroxyalkyl of 2 or 3 carbon atoms, alkoxyalkyl of a total of 3 to 8 carbon atoms or β-cyanoethyl, X is cyano, carbamoyl or CONHR, and Y is hydrogen, or X and Y together are

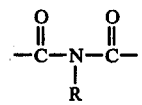

and Z is $\diagdown$N—R or —S—.

7. A compound as claimed in claim 1, of the formula

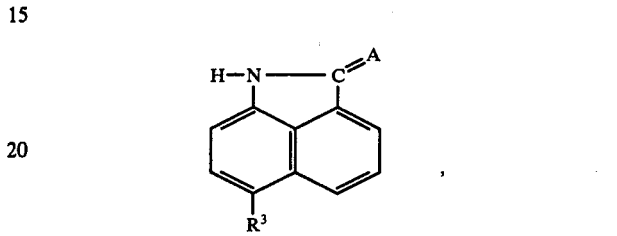

where $R^3$ is hydrogen, chlorine, bromine, methoxy, ethoxy, phenylmercapto, benzoyl, phenylmercapto or benzoyl substituted by chlorine, methyl or methoxy, methylsulfonyl, acetyl, propionyl or sulfamoyl which is monosubstituted or disubstituted by alkyl of 4 to 8 carbon atoms, and A is

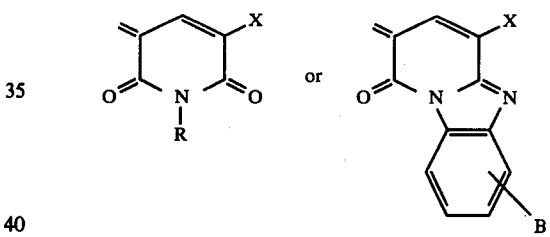

and R and B have the meanings given in claim 6.

8. A compound as claimed in claim 1, of the formula

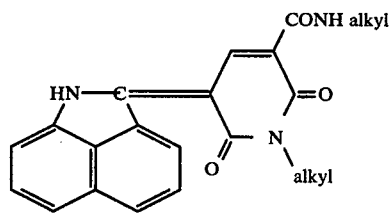

where alkyl is of 2 to 4 carbon atoms.

9. A compound as claimed in claim 1, of the formula

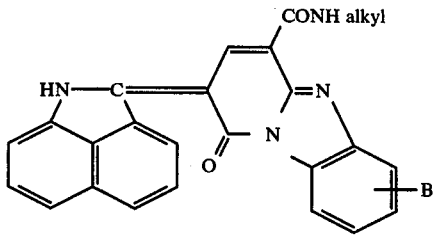

where alkyl is of 3 to 8 carbon atoms or is hydroxyalkyl or alkoxyalkyl of a total of 2 to 8 carbon atoms and B has the stated meanings.

10. A compound as claimed in claim 1 wherein A is

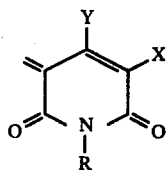

wherein X, Y and R have the stated meanings.

11. A compound as claimed in claim 1 wherein A is

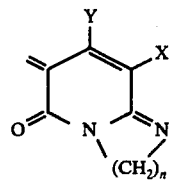

wherein X, Y and n have the stated meanings.

12. A compound as claimed in claim 1 wherein A is

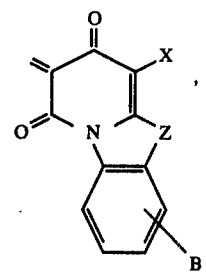

wherein X, Z and B have the stated meanings.

13. A compound as claimed in claim 1 wherein A is

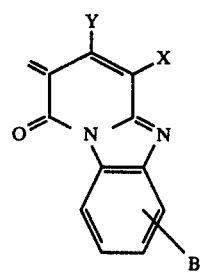

wherein X, Y and B have the stated meanings.

* * * * *

UNITED STATES PATENT AND TRADEMARK OFFICE
CERTIFICATE OF CORRECTION

PATENT NO. : 4,096,145
DATED : June 20, 1978
INVENTOR(S) : ERNST SCHEFCZIK

It is certified that error appears in the above—identified patent and that said Letters Patent are hereby corrected as shown below:

Column 43, line 35, delete "and Z is $>$N-R or -S-"

Column 44, line 10, delete "and Z is $>$N-R or -S-"

Signed and Sealed this

Second Day of January 1979

[SEAL]

Attest:

RUTH C. MASON
Attesting Officer

DONALD W. BANNER
Commissioner of Patents and Trademarks